United States Patent
Gaida et al.

(10) Patent No.: US 7,708,404 B2
(45) Date of Patent: May 4, 2010

(54) OPHTHALMOLOGIC SURGICAL WORK STATION

(75) Inventors: Gerhard Gaida, Aalen (DE); Gundel Papke, Lossow (DE); Jana Gieske, Aalen (DE); Delbert Peter Andrews, Oberkochen (DE); Christian Müller, Langenau (DE); Werner Nahm, Bühlerzell (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 276 days.

(21) Appl. No.: 11/826,154

(22) Filed: Jul. 12, 2007

(65) Prior Publication Data

US 2008/0013048 A1  Jan. 17, 2008

(30) Foreign Application Priority Data

Jul. 14, 2006  (DE)  ........................ 10 2006 033 054

(51) Int. Cl.
*A61B 3/13* (2006.01)
(52) U.S. Cl. ..................................................... 351/205
(58) Field of Classification Search ................ 351/205, 351/208, 209, 210, 211, 212; 248/287.1
See application file for complete search history.

(56) References Cited

U.S. PATENT DOCUMENTS

| 3,809,454 | A | | 5/1974 | Brambring |
|---|---|---|---|---|
| 4,854,301 | A | | 8/1989 | Nakajima |
| 4,912,388 | A | * | 3/1990 | Tanaka et al. ............... 318/640 |
| 5,098,426 | A | | 3/1992 | Sklar et al. |
| 5,413,555 | A | | 5/1995 | McMahan |
| 5,590,060 | A | * | 12/1996 | Granville et al. ............ 702/155 |
| 6,962,581 | B2 | * | 11/2005 | Thoe ............................ 606/1 |
| 2005/0039567 | A1 | | 2/2005 | Peterson et al. |

FOREIGN PATENT DOCUMENTS

| DE | 1 491 094 | 5/1969 |
|---|---|---|
| WO | WO 00/00253 | 1/2000 |

OTHER PUBLICATIONS

German Office Action Jun. 2007.

* cited by examiner

*Primary Examiner*—Scott J Sugarman
*Assistant Examiner*—Tuyen Q Tra
(74) *Attorney, Agent, or Firm*—Walter Ottesen

(57) ABSTRACT

An ophthalmologic surgical work station has a microscope and a foot switch corresponding thereto. The microscope is connected to the foot switch via a console. The microscope and the foot switch are coarsely prepositioned and a change of the relative position between the microscope and the foot switch with respect to each other is only possible via a fine positioning.

16 Claims, 4 Drawing Sheets

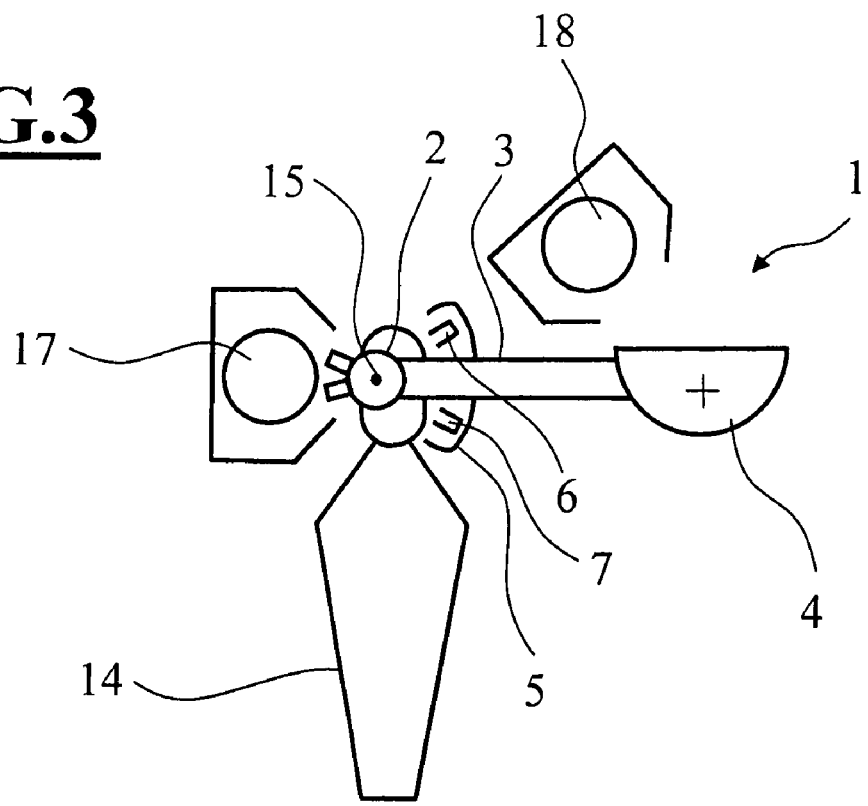
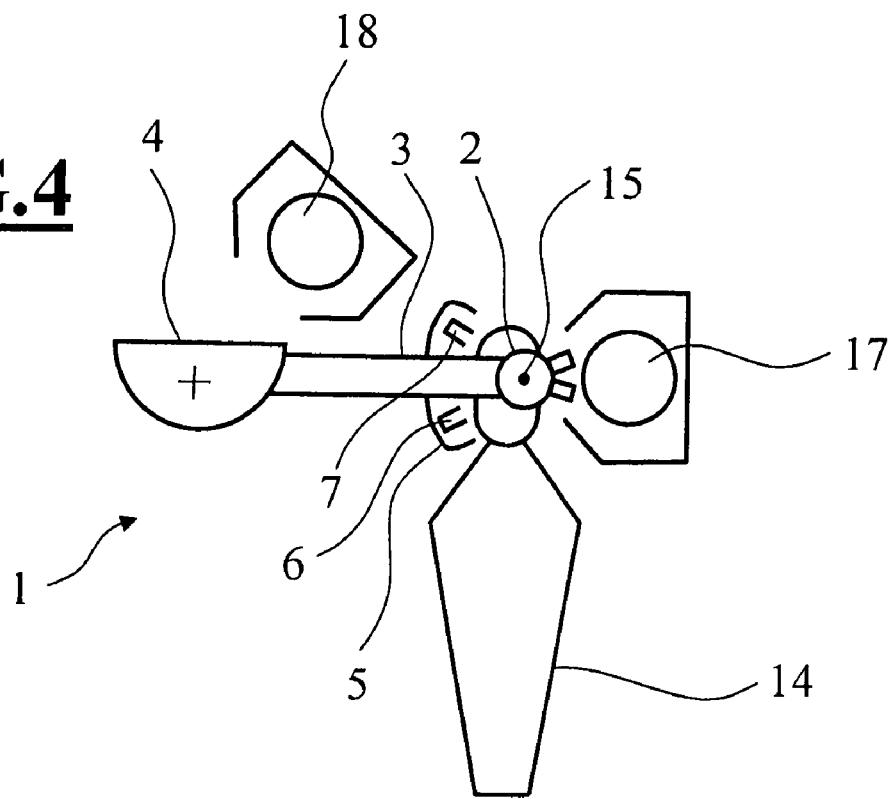

OPHTHALMOLOGIC SURGICAL WORK STATION

CROSS REFERENCE TO RELATED APPLICATION

This application claims priority of German patent application no. 10 2006 033 054.4, filed Jul. 14, 2006, the entire content of which is incorporated herein by reference.

FIELD OF THE INVENTION

The invention relates to an ophthalmologic surgical work station having a microscope and a corresponding first foot switch. The microscope is connected to the foot switch via a console.

BACKGROUND OF THE INVENTION

It is conventional to utilize many highly developed apparatus in surgical procedures in eye surgery. Great care, much experience and a high measure of caution by persons working in the operating room are required in order to achieve a high level of safety. This concerns, inter alia, connecting elements between the individual apparatus such as connecting cables, hoses and the like. It is of importance that in an operating room: for example, none of the persons active there trip over such connecting elements; no insert connection is lost because of an unwanted hand movement or two connecting elements, which do not belong to each other, are coupled to each other. In addition to the danger of an accident in the operating room, there also is the additional danger that a surgical success cannot be obtained for the patient because of such unwanted actions.

The complexity of the apparatus to be used in a surgical procedure on the eye leads to the situation that much time must be expended in order to ensure the high measure of care and caution during an operation. While a cataract operation mostly only requires approximately 15 minutes of surgery time, a similarly long time span must be provided for the preparatory measures and the safety measures. If these accompanying measures would take less time, then more surgical procedures can be carried out in a work shift and a higher productivity can be obtained.

SUMMARY OF THE INVENTION

It is therefore an object of the invention to provide a work station with which more surgical procedures per work shift can be achieved while at the same time providing the same high level of work safety and preferably still higher level of work safety. It is also an object of the invention to provide an ophthalmologic surgical work station whereat a surgeon must carry out fewer time intensive ancillary activities and fewer manipulations so that, overall, a more relaxed work activity is possible during surgery and an overall work shift.

The ophthalmologic surgical work station of the invention includes: a foot switch; a console; a microscope connected to the foot switch via the console; the microscope and the foot switch being coarsely prepositioned relative to each other; and, the work station being so configured that a change of the relative position between the microscope and the foot switch with respect to each other is only possible with a fine positioning.

The ophthalmologic surgical work station according to the invention includes a microscope and a corresponding first foot switch. The microscope is connected to the foot switch via a console. The microscope and the first foot switch are coarsely prepositioned and a change of the relative position between microscope and first foot switch with respect to each other is possible only via a fine positioning. In this way, the degree of freedom and the space for movement of the microscope and of the first foot switch are greatly limited so that a time intensive prepositioning is no longer required. The apparatus associated with each other, such as microscope and first foot switch, are already at a position suitable for the surgeon. A fine positioning is only required for an individual setting depending upon the surgeon. The plurality of adjusting possibilities for a microscope and a foot switch as they are possible in the state of the art are considerably reduced in accordance with the invention. A prepositioning of a microscope mounted, for example, on the ceiling of the operating room and a foot switch assembly freely movable in space are no longer necessary. The fine positioning permits only a small space of movement for the microscope and the first foot switch. This means that the apparatus are only present where a surgeon needs and expects the same so that the danger of an accident and the space potentially taken up in the operating room are reduced. In this way, the attention of the personnel, which are active in the operating room during a surgical procedure, can be directed with greater intensity to the additional apparatus and the actual eye operation.

According to a preferred embodiment of the invention, the microscope is connected to the console via a holding arm projecting outwardly from the console. An outwardly extending holding arm makes it possible that sufficient distance is achieved between microscope and console in order to arrange a patient on a patient cot directly under the microscope. The console is then provided laterally on the patient cot whereas the microscope can be placed directly over the eye to be operated upon by means of the holding arm.

Preferably, the holding arm is displaceable in the vertical. In this way, differently high patient cots can be used and the microscope can be adjusted in elevation so that a surgeon can work therewith in a relaxed manner. A contribution to the ergonomics of the ophthalmologic surgical work station is provided in that the holding arm is displaceable in the vertical.

Preferably, the console, which connects the microscope to the first foot switch, is configured as a tower. In this way, the console assumes the function to provide the elevation difference between foot switch assembly and the microscope. A holding arm, on which the microscope is attached, can thereby be so configured that it, for example, only projects as an essentially horizontal part from the console. This makes possible a relatively simple and slim configuration of the component group comprising console and holding arm with the microscope.

It is advantageous when the console has at least one additional apparatus which is selected from the group which includes a phacoemulsification apparatus, a vitrectonomy apparatus, a laser coagulation apparatus, an endoilluminator and a video apparatus. Each additional apparatus is provided with an additional foot switch. Other additional apparatus which are needed for ophthalmology can be provided in the console. In this way, it is achieved that, in addition to the console, no such additional apparatus need be positioned. Connecting cables, connections, hoses and the like are completely accommodated within the console. This considerably improves the work station's safety and reduces the danger of accident while, at the same time, the space in the operating room, which is taken up by the apparatus, can be reduced to a minimum. The space available for the personnel in the operating room can thereby be considerably increased. With the integration of one or several additional apparatus in a console, it is possible to provide a unitary operator control. Becoming familiar with the manipulations of the apparatus having the same manipulation philosophy can thereby be shortened in comparison to the manipulation of several individual apparatus having different manipulation philosophies. Furthermore, some components can be saved thereby which are required for operating a microscope and at least one additional apparatus. It is, for example, possible that only a central control, a network part, an underframe, an electronic connection and a data connection for the operation of the ophthalmologic surgical work station are required. This reduces the number of fault possibilities and makes possible a cost effective construction.

It is especially advantageous when the first foot switch and the additional foot switch of an additional apparatus are arranged on a common foot switch assembly. On the one hand, the required space in an operating room is reduced compared to the space that several individual foot switch assemblies require. On the other hand, double and multiple connecting lines are saved and can be integrated into a single line. For the surgeon too, it is simpler to manipulate several foot switches on only a single foot switch assembly. The danger of activating the wrong switch is reduced and additionally, the unitary manipulation philosophy of the several foot switches can be provided compared to the state of the art. The combination of a console having a microscope coupled thereto and at least one of the above-mentioned additional apparatus as well as a common foot switch assembly increases the integration density of the ophthalmologic surgical work station.

When the first foot switch and the corresponding additional foot switch are displaceable on the foot switch assembly and are arranged so as to be positionable with respect to each other, an individual adaptation to the particular surgeon can be obtained. Nevertheless, this is only a fine positioning of the particular foot switch. With the arrangement of the foot switches on a common foot switch assembly, the foot switches are already coarsely prepositioned. A search, arrangement and securing of the particular foot switch as it is required in solutions of the state of the art are unnecessary in such an embodiment.

For still higher ergonomics of the ophthalmologic surgical work station, the foot switch assembly and the microscope are configured movable to the console. This can be provided in the horizontal as well as in the vertical directions. Preferably, the foot switch assembly and the microscope are configured so as to be pivotable about the console. In this way, it is possible to pivot the foot switch assembly and the microscope, for example, by 180° so that the console with a possible additional apparatus no longer has to be arranged to the right but to the left of a patient cot. In this way, a high flexibility with respect to a positioning of the ophthalmologic surgical work station in an operating room is achieved. For tight space relationships in an operating room, an optimal arrangement of the ophthalmologic surgical work station and of the seating as suited for the surgeon are achieved.

Furthermore, it is possible that the microscope and the console are configured to be pivotable about the foot switch assembly. The foot switch assembly can be fixedly mounted to be stationary in the operating room so that a still higher flexibility in the arrangement of the ophthalmologic surgical work station can be achieved in an operating room.

Preferably, the foot switch assembly is configured to be pivotable. In this way, it is possible that a surgeon can carry out a surgical procedure longitudinally of as well as transversely to the patient cot (temporal or superior). The foot switch assembly is then adjustable into the position suitable for the selected surgery position. In this context, it is practical when the microscope and the foot switch assembly are displaceable in at least two predetermined positions. In this way, the surgeon, for example, can carry out the operation on the left side or right side of the patient.

Preferably, the foot switch assembly is connected to the console by means of an arm adjustable in the longitudinal direction. This makes possible a still higher adaptation to the individual conditions of a surgeon and increases the ergonomics of the work station.

Preferably, the work station has a monitor and/or a manipulable video screen. An assistant present in the operating room can thereby monitor and check the most important data during a surgical procedure. In advance of the surgical procedure, specific profiles for a surgeon or a patient can be inputted. This can be concerned with the following: a microscope magnification, a maximum pressure in the supply of a rinsing liquid, a maximum energy for a high frequency actuator of a phacoemulsification apparatus, a light intensity in a microscope, filter settings or adjustments of a foot switch assembly.

Preferably, the microscope holding arm, the console, the arm and the foot switch assembly form essentially a C-shaped configuration. In this way, a patient cot with a patient can be positioned above the foot switch assembly with the arm and below the holding arm and microscope.

BRIEF DESCRIPTION OF THE DRAWINGS

The invention will now be described with reference to the drawings wherein:

FIG. 3 is a schematic of an ophthalmologic surgical work station in plan view wherein the holding arm and the foot switch assembly are arranged in a first position;

FIG. 4 is a schematic of an ophthalmologic surgical work station in a plan view wherein the holding arm and the foot switch assembly are arranged in a second position;

DESCRIPTION OF THE PREFERRED
EMBODIMENTS OF THE INVENTION

Figure 1:
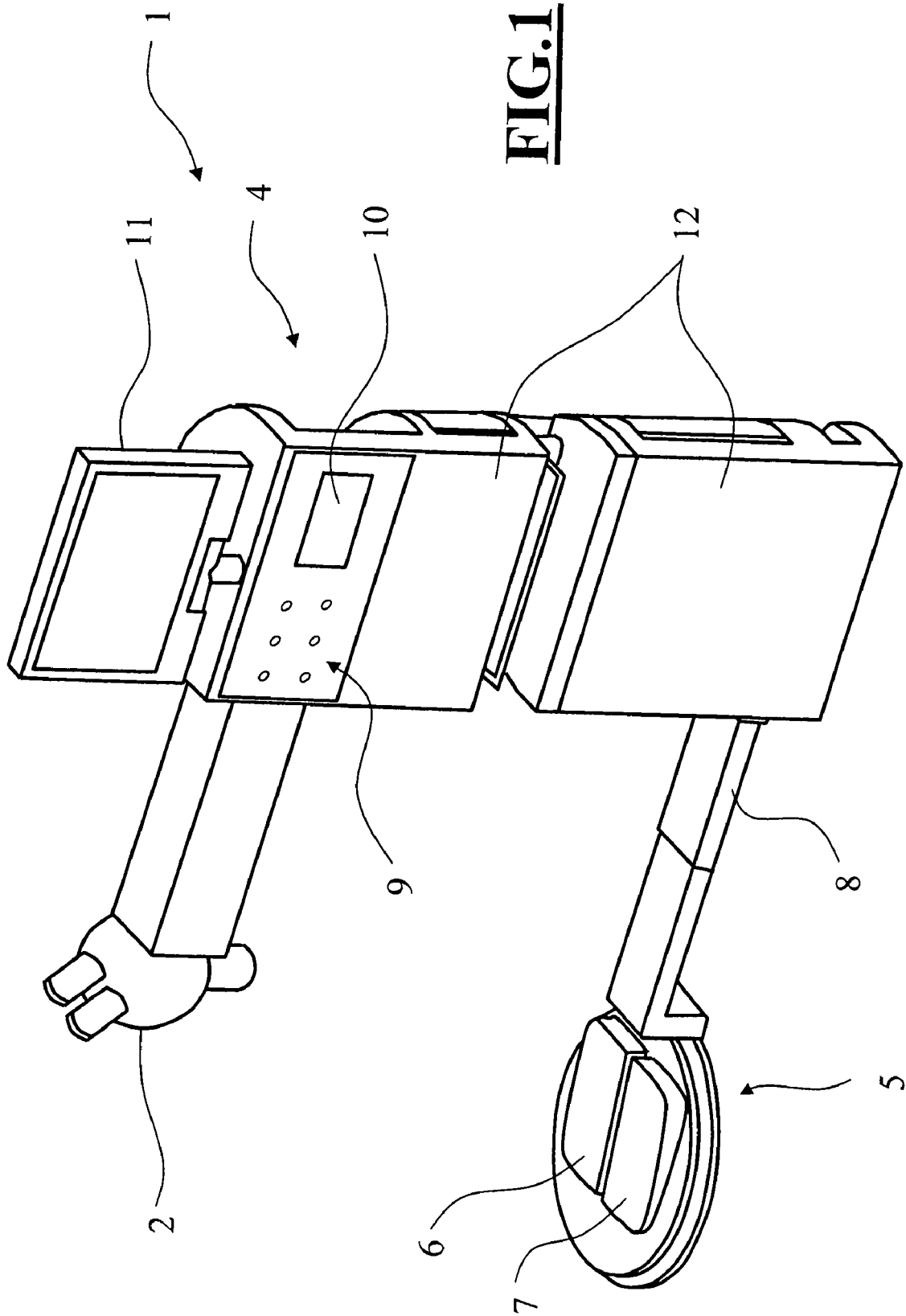
FIG. 1 is a schematic perspective front view of an ophthalmologic surgical work station according to the invention.

FIG. 1 shows a schematic of an ophthalmologic surgical work station 1 in a perspective front view. The work station 1 includes a microscope 2 which is, for example, a stereoscopic microscope having an illumination unit. The microscope is attached to a holding arm 3 which is coupled to a console 4. The console 4 is configured as a tower and a plurality of apparatus can be integrated into the console. The work station 1 further includes a foot switch assembly 5 which has a first foot switch 6 and a second foot switch 7. In another embodiment than that shown in FIG. 1, the foot switch assembly can have additional foot switches. The foot switch assembly is coupled to the console 4 via a foot switch assembly arm 8. The arm 8 can be adjustable telescopically with respect to its length. In this way, it is possible to arrange the foot switch assembly 5 in a position wanted by a surgeon.

For example, a phacoemulsification apparatus can be integrated into the console 4. In such an apparatus, an irrigation and aspiration unit is provided so that a rinsing liquid can be supplied to the eye under surgery and eye lens fragments including the rinse liquid can again be drawn off by suction. Connections for such rinsing and suction lines can, for example, be provided in a connection field 9 which is generally provided for removable sterile apparatus components. In addition to hose connections, connections can be provided, for example, for an illumination which is required for a vitrectonomy treatment. Furthermore, the connection field 9 can be prepared generally for electrical and optical connections. The connection field 9 is placed next to an exchangeable cassette 10 for a pump device in the console 4. The connection field 9 as well as the exchangeable cassette 10 are preferably placed relatively far up in the console 4. This is advantageous for the operator control of the ophthalmologic surgical work station 1.

Supply component groups 12 with electronics and optical units are integrated into the console 4 below the connection field 9. A monitor 11 is mounted above the console 4 and can simultaneously have a manipulable video screen. The monitor is so arranged in the embodiment shown in FIG. 1 that an assistant working in the operating room can view the same and operate the same easily. An image which, for example, is viewed in the microscope 2, can be displayed on the monitor 11. In addition, it is possible to set parameters, which are specific for an eye operation, with the operator-controlled image screen (touch screen). The parameters can be pregiven by a surgeon or generally via the type of surgery. For example, it is possible to provide a computer program with which a specific set of data can be stored for a first surgeon. If another surgeon takes over the work at such a work station, another set of data can be programmed and/or called up which is suitable for this other surgeon. The foregoing can be concerned with a presetting of the magnification of the microscope, a specific light intensity and a specific filter setting for the illumination of the area of surgery. Additional parameters can be: pressure values for a suction or rinsing line; the energy made available for an ultrasonic transducer; or, pulse forms for driving an actuator.

Figure 2:
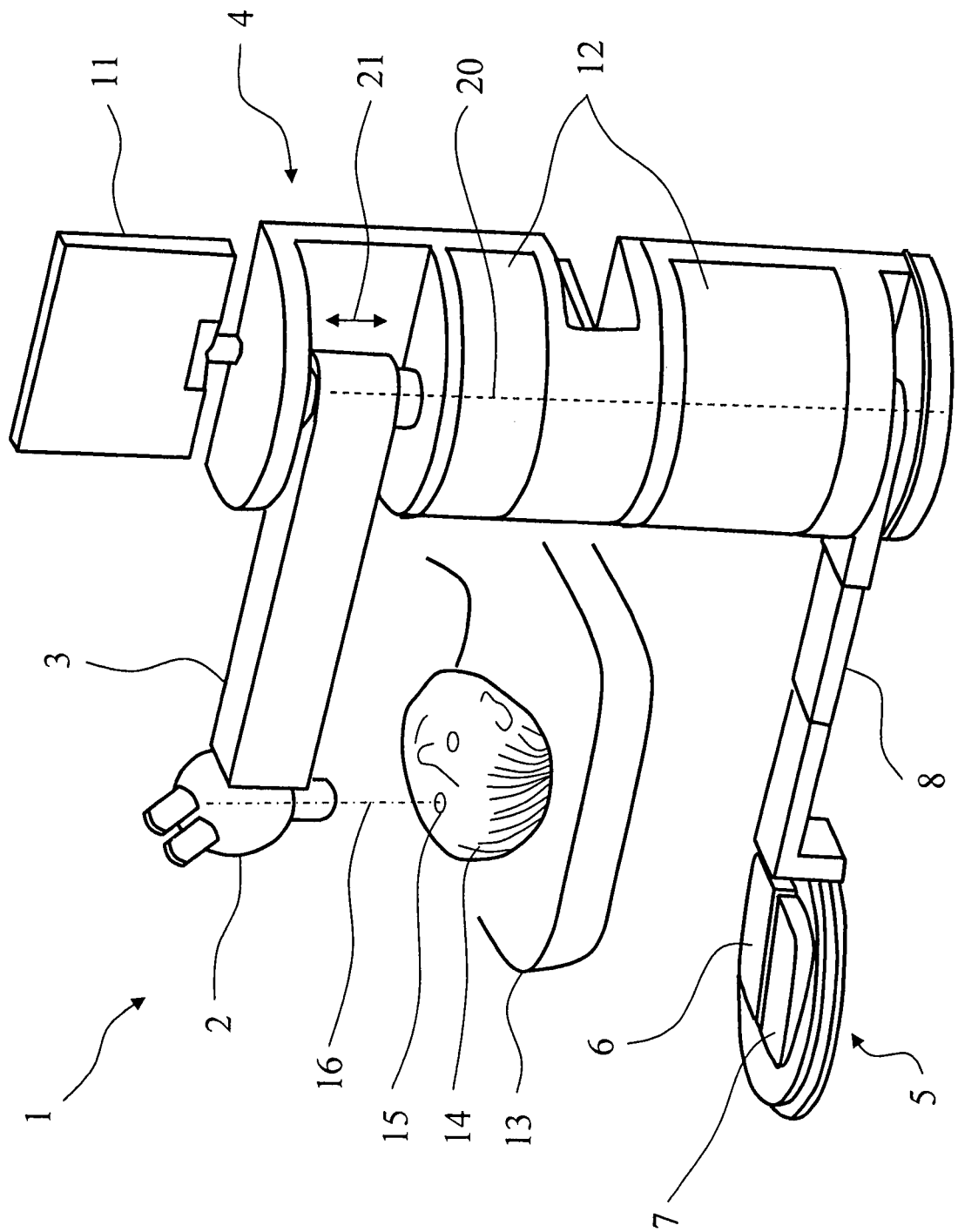
FIG. 2 is a schematic perspective rear view of the ophthalmologic surgical work station of FIG. 1.

A free space is provided below the microscope 2 and the holding arm 3. This space can be partially filled out by a patient cot having a patient lying thereon. In FIG. 2, a patient cot 13 is indicated on which a patient 14 lies in such a manner that the left eye 15 of the patient is disposed directly in the beam path 16 of the microscope 2. To precisely align the beam path 16 of the microscope 2 with the eye 15 of the patient 14, only an adjustment of the holding arm 3 in the vertical direction is provided (see arrow 21 in FIG. 2) in the embodiment as shown in FIGS. 1 and 2. A variation of the length of the holding arm 3 is not possible. An alignment in horizontal direction takes place exclusively by means of the patient cot 13.

The length of the holding arm 3 and of the microscope 2 attached thereto indicates the position for a surgeon. The foot switch assembly 5 is then correspondingly so positioned via the foot switch assembly arm 8 that the surgeon can sit relaxed and can see through the microscope 2. The cables for the foot switch assembly 5 run, for example, within the arm 8. It is advantageous when this setting between microscope 2 and foot switch assembly 5 is especially determined for each surgeon and is subsequently fixed. Attention is called to the fact that the telescopic adjustment possibility of the arm 8 shown in FIGS. 1 and 2 is much too large for the practical embodiment. The distance of the foot switch assembly 5 to the console 4 is actually considerably less than the distance of the microscope 2 to the console 4. This position is pregiven by the prepositioning and for a fine positioning, only small adjustments can still be carried out.

An alignment of the work station 1 with respect to an eye 15, which is to be operated upon, is possible in the horizontal direction exclusively by means of the cot 13. By limiting the degrees of freedom and the movement spaces for the microscope, console and foot switch assembly, time is saved in order to coarsely preposition the apparatus with respect to each other. This criterion is especially of importance because, for example, a cataract surgical procedure usually takes only approximately 15 minutes so that the time savings of a few minutes for a no longer required prepositioning of the apparatus used leads to a savings of time which can be used for additional surgical procedures. In this way, a higher productivity in the operating room is obtained with the use of an ophthalmologic surgical work station according to the invention.

In the schematic plan view of FIG. 3, the arrangement between the ophthalmologic surgical work station 1, patient 14 and surgeon 17 is shown. The work station 1 has a console 4 from which a holding arm 3 projects. At the distal end of the holding arm 3, a microscope 2 is mounted and the eye 15 of the patient 14, which is to be operated on, lies in the beam path of the microscope. It is noted that the eye 15 is not visible in the plan view of FIG. 3 but is shown here for the purpose of explanation. The surgeon 17 is seated laterally of the patient cot 13 and can operate a foot switch assembly 5 having the foot switches 6 and 7. As shown in FIG. 2, the holding arm 3 and the foot switch assembly arm 8 with the foot switch assembly 5 can be pivoted about an axis 20 within the console 4.

In FIG. 4 an arrangement is shown wherein the console 4 is shown having an unchanged position compared to the arrangement of FIG. 3; whereas, the holding arm 3 and the foot switch assembly 5 have been pivoted about the console 4 by 180°. With this arrangement, the surgeon can work in a mirror image with respect to the arrangement shown in FIG. 3. This arrangement can, for example, be selected when a surgical procedure is not provided for the right eye (see FIG. 3) but on the left eye of the patient 14. Another reason for the different positions of the microscope 2 and the foot switch assembly 5 with respect to the console 4 can be tight space conditions in an operating room. It should be further noted that an assistant 18 can monitor relevant data on a monitor during a surgical procedure or can undertake a specific manipulation on the console 4. In the arrangement shown in FIG. 4, the assistant 18 has to be able to move on the left side of the patient cot and forward of the patient cot. In the arrangement shown in FIG. 3, the assistant 18 has to be able to move on the right side of the patient cot and forward of the patient cot. In this way, the work station 1 can be arranged in dependence upon the work sequence and the spatial limitations in the operating room.

Figure 5:
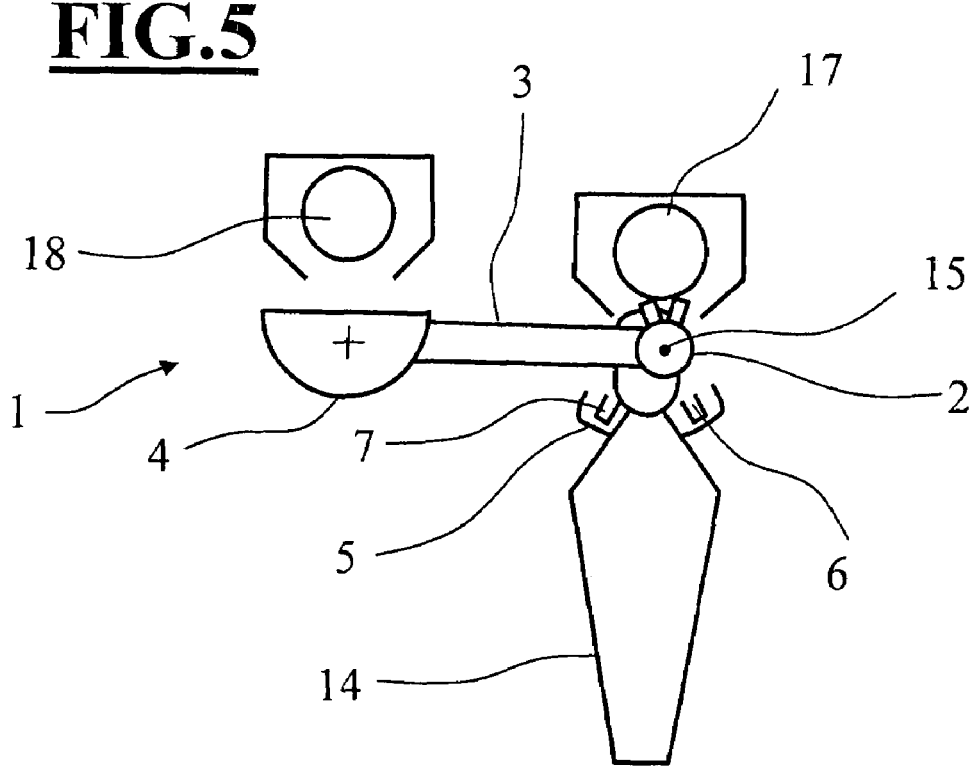
FIG. 5 is a schematic of an ophthalmologic surgical work station of FIG. 4 wherein the microscope and the foot switch assembly are arranged in a third position; and, FIG. 6 is a schematic of an ophthalmologic surgical work station viewed in plan wherein microscope and foot switch assembly are arranged in a fourth position.

In FIG. 5, a further arrangement of the work station is shown. The surgeon 17 is not positioned laterally (temporal) to the patient cot 13 but positioned in the extension of the head end of the patient cot 13 (superior). The foot switch assembly 5 is configured to be pivotable about its own axis so that the foot switch assembly 5 can be controlled also in this arrangement.

Figure 6:
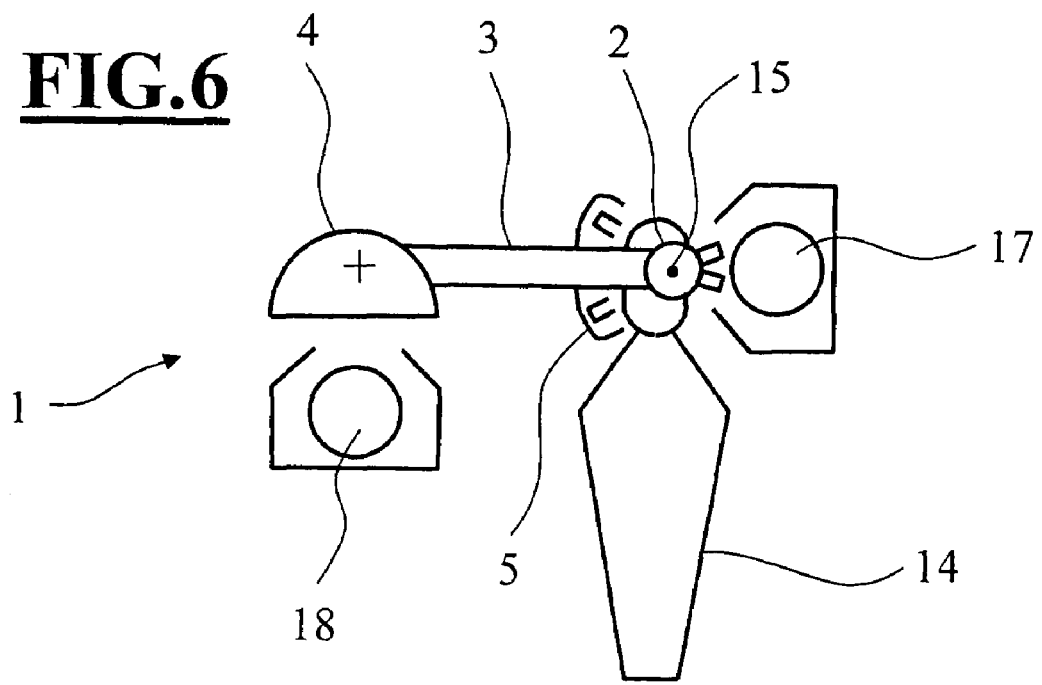

In FIG. 6, a further possibility for the arrangement of a work station 1 is shown. In this embodiment, the foot switch assembly 5 is spatially fixed on the floor so that the console 4 with the holding arm 3 and the microscope 2 are movable about the foot switch assembly 5. In this arrangement, the assistant 18 can be next to the patient cot 13 and simultaneously operate the monitor and/or touch screen 11 as well as the console 4. Data, which can be seen on the monitor 11, or general parameters for the operation of the work station, can be introduced via a corresponding device also for the surgeon into the microscope field of view. In this way, the surgeon can look through the microscope without interruption during a surgical procedure and need not look up to the monitor for controlling specific data and thereby interrupt the surgical procedure.

It is understood that the foregoing description is that of the preferred embodiments of the invention and that various changes and modifications may be made thereto without departing from the spirit and scope of the invention as defined in the appended claims.

What is claimed is:

1. An ophthalmologic surgical work station comprising:
   a foot switch;
   a console;
   a microscope connected to said foot switch via said console;
   an adjustable arm connecting said foot switch to said console to coarsely preposition said microscope and said foot switch relative to each other so as to ensure that said microscope and said foot switch are already prepositioned for an eye surgeon in advance of a surgical procedure at said work station; and,
   said work station being so configured that a change of the relative position between said microscope and said foot switch with respect to each other is only possible with a fine positioning.

2. The ophthalmologic surgical work station of claim 1, further comprising a holding arm projecting from said console; and, said microscope being connected to said console via said holding arm.

3. The ophthalmologic surgical work station of claim 2, wherein said holding arm is movable in the vertical.

4. The ophthalmologic surgical work station of claim 3, wherein said console is configured to have a tower-like shape.

5. The ophthalmologic surgical work station of claim 1, wherein said foot switch is a first foot switch; said console includes at least one ancillary apparatus selected from the group comprising: a phacoemulsification apparatus; a vitrectonomy apparatus; a laser coagulation apparatus; an endoilluminator; and, a video unit; and, said work station further comprises at least a second foot switch corresponding to said one ancillary apparatus.

6. The ophthalmologic surgical work station of claim 5, wherein said first and second foot switches conjointly define a common foot switch assembly.

7. The ophthalmologic surgical work station of claim 6, wherein said first and second foot switches are displaceable and positionable relative to each other on said foot switch assembly.

8. The ophthalmologic surgical work station of claim 6, wherein said foot switch assembly and said microscope are movable relative to said console.

9. The ophthalmologic surgical work station of claim 6, wherein said foot switch assembly and said microscope are pivotable about said console.

10. The ophthalmologic surgical work station of claim 6, wherein said microscope and said console are configured to be pivotable about said foot switch assembly.

11. The ophthalmologic surgical work station of claim 6, wherein said foot switch assembly is pivotable about its own axis.

12. The ophthalmologic surgical work station of claim 6, wherein said microscope and said foot switch assembly are displaceable into at least two predetermined positions.

13. The ophthalmologic surgical work station of claim 6, wherein said arm is adjustable in length so as to permit said foot switch assembly to be finely adjusted in position relative to said console to adapt the foot switch assembly to the conditions of the individual eye surgeon thereby ensuring the comfort of the eye surgeon during the surgical procedure.

14. The ophthalmologic surgical work station of claim 6, further comprising a holding arm projecting from said console; said microscope being connected to said console via said holding arm; and, said microscope holding arm, said console, said length-adjustable arm and said foot switch assembly conjointly defining a C-shape configuration when viewed in side elevation.

15. The ophthalmologic surgical work station of claim 6, wherein said arm is a rigid arm adjustable in length so as to permit said foot switch to be finely adjusted in position relative to said console to adapt the foot switch to the conditions of the individual eye surgeon thereby ensuring the comfort of the eye surgeon during the surgical procedure.

16. The ophthalmologic surgical work station of claim 1, further comprising a monitor and/or a manipulative video screen.

* * * * *